(12) United States Patent
Tsukamoto et al.

(10) Patent No.: US 11,760,739 B2
(45) Date of Patent: Sep. 19, 2023

(54) METHOD OF PRODUCING 3-HYDROXYADIPIC ACID-3,6-LACTONE

(71) Applicant: Toray Industries, Inc., Tokyo (JP)

(72) Inventors: Daijiro Tsukamoto, Kamakura (JP); Kenji Kawamura, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 210 days.

(21) Appl. No.: 17/439,782

(22) PCT Filed: Mar. 24, 2020

(86) PCT No.: PCT/JP2020/012855
§ 371 (c)(1),
(2) Date: Sep. 15, 2021

(87) PCT Pub. No.: WO2020/196459
PCT Pub. Date: Oct. 1, 2020

(65) Prior Publication Data
US 2022/0185786 A1  Jun. 16, 2022

(30) Foreign Application Priority Data
Mar. 25, 2019  (JP) ................................. 2019-056708

(51) Int. Cl.
*C07D 307/33*  (2006.01)

(52) U.S. Cl.
CPC .................................. *C07D 307/33* (2013.01)

(58) Field of Classification Search
CPC .................................................... C07D 307/33
See application file for complete search history.

(56) References Cited

U.S. PATENT DOCUMENTS

| | | | |
|---|---|---|---|
| 4,886,889 A | 12/1989 | Mattison et al. | |
| 10,196,352 B2 * | 2/2019 | Ito | ............................. B01J 23/44 |
| 11,149,001 B2 * | 10/2021 | Tsukamoto | ........... B01J 23/8474 |
| 2011/0003355 A1 | 1/2011 | Clark et al. | |
| 2014/0322777 A1 | 10/2014 | Clark et al. | |
| 2015/0259311 A1 | 9/2015 | Lee et al. | |
| 2017/0320819 A1 | 11/2017 | Ito et al. | |
| 2018/0142271 A1 | 5/2018 | Isobe et al. | |
| 2019/0112247 A1 | 4/2019 | Clark et al. | |
| 2019/0276860 A1 | 9/2019 | Isobe et al. | |
| 2021/0002194 A1 | 1/2021 | Clark et al. | |

FOREIGN PATENT DOCUMENTS

| | | |
|---|---|---|
| CA | 3 046 130 | 6/2018 |
| JP | 53-68768 A | 6/1978 |
| JP | 62-201606 A | 9/1987 |
| JP | 62-277349 A | 12/1987 |
| JP | 2010-95450 A | 4/2010 |
| JP | 2012-59 A | 1/2012 |
| JP | 2012-115237 A | 6/2012 |
| JP | 2012-528885 A | 11/2012 |
| JP | 2015-119738 A | 7/2015 |
| JP | 2017-51117 A | 3/2017 |
| WO | 2016/068108 A1 | 5/2016 |
| WO | 2016/199856 A1 | 12/2016 |
| WO | 2017/011407 | 1/2017 |
| WO | 2017/209102 A1 | 12/2017 |

OTHER PUBLICATIONS

Kato, Y. et al., "A convenient synthesis of γ-carboxymethlbutanolide," *Synthetic Communications*, 1977, 7(2), pp. 125-130.
Capraro, H.-G. et al., "Synthesis and biological activity of 2-lactonyl penems," *The Journal of Antibiotics*, 1988, 41(6), pp. 759-770.
Hagen, A. et al., "Engineering a Polyketide Synthase for In Vitro Production of Adipic Acid," *ACS Synthetic Biology*, 2016, 5(1), pp. 21-27.
Allan, R. D. et al., "Synthesis of Analogues of GABA. IX 5-(Aminomethyl)-3-hydroxyfuran-2(5H)-one," *Australian Journal of Chemistry*, 1983, 36(5), pp. 977-981.
Extended European Search Report dated Oct. 27, 2022, of counterpart European Application No. 20777505.7.

* cited by examiner

*Primary Examiner* — Golam M Shameem
(74) *Attorney, Agent, or Firm* — DLA Piper LLP (US)

(57) ABSTRACT

A method relates to producing 3-hydroxyadipic acid-3,6-lactone, the method including the following steps (A) and (B): (A) a step of adding an acid to a 3-hydroxyadipic acid-containing aqueous solution to obtain a 3-hydroxyadipic acid-3,6-lactone-containing aqueous solution; and (B) a step of obtaining a 3-hydroxyadipic acid-3,6-lactone extract by bringing the 3-hydroxyadipic acid-3,6-lactone-containing aqueous solution obtained in step (A) into contact with an extraction solvent that is phase-separated from the solution.

6 Claims, No Drawings

METHOD OF PRODUCING 3-HYDROXYADIPIC ACID-3,6-LACTONE

TECHNICAL FIELD

This disclosure relates to a method of producing 3-hydroxyadipic acid-3,6-lactone from a 3-hydroxyadipic acid-containing aqueous solution.

BACKGROUND

3-Hydroxyadipic acid is a dicarboxylic acid having a carbon number of 6 and having a hydroxyl group at the β-position. As for use of 3-hydroxyadipic acid, WO 2016/068108 describes that it serves as a raw material for the synthesis of ε-caprolactam.

With respect to the method of recovering 3-hydroxyadipic acid from a 3-hydroxyadipic acid-containing aqueous solution, WO 2016/199856 describes that at the time of recovering 3-hydroxyadipic acid from the 3-hydroxyadipic acid-containing aqueous solution obtained by synthesizing 3-hydroxyadipic acid by microbial fermentation, column chromatography, ion-exchange chromatography, crystallization, distillation and the like can be used. In addition, JP-A-2012-115237 describes a method where at the time of recovering an aliphatic dicarboxylic acid such as 3-hydroxyadipic acid from an aliphatic dicarboxylic acid-containing aqueous solution, the aliphatic dicarboxylic acid is extracted into a solvent that is phase-separated from the aqueous solution, and the aliphatic dicarboxylic acid is thereby recovered.

Also, WO 2016/068108 describes a method where a sulfuric acid is added to a 3-hydroxyadipic acid-containing aqueous solution and the aqueous solution is evaporatively concentrated and then separated by column chromatography to thereby synthesize 3-hydroxyadipic acid-3,6-lactone, and it is described that, as with 3-hydroxyadipic acid, 3-hydroxyadipic acid-3,6-lactone also serves as a raw material for the synthesis of ε-caprolactam. Although we are not aware of literature specifically disclosing a method of recovering 3-hydroxyadipic acid-3,6-lactone, JP-A-2012-000059 describes a method of recovering muconolactone that is close to 3-hydroxyadipic acid-3,6-lactone in terms of chemical structure, and, specifically, describes a method where at the time of recovering muconolactone from a muconolactone-containing aqueous solution obtained by synthesizing muconolactone by microbial fermentation, hydrochloric acid is added to the muconolactone-containing aqueous solution and muconolactone is then extracted into ethyl acetate and thereby recovered.

When using 3-hydroxyadipic acid as a raw material of ε-caprolactam, according to WO 2016/068108, 3-hydroxyadipic acid that is not contained in the solution is preferably used to serve as a raw material for the synthesis of ε-caprolactam, because the reaction form or reaction solvent can be appropriately selected. Out of the methods described in WO 2016/199856 as the method of recovering 3-hydroxyadipic acid, the methods using column chromatography and ion-exchange chromatography are industrially disadvantageous in that the large-scale processing is uneconomical and, in addition, since the water solubility and boiling point of 3-hydroxyadipic acid are very high, recovery by crystallization or distillation is also improper. The method of recovering an aliphatic dicarboxylic acid by the extraction described in JP-A-2012-115237 can hardly be applied, because water solubility of 3-hydroxyadipic acid is very high (see, Comparative Reference Example 2 below). In this way, it has been difficult for known techniques to recover 3-hydroxyadipic acid serving as an ε-caprolactam synthesis raw material from a 3-hydroxyadipic acid-containing aqueous solution.

On the other hand, WO 2016/068108 describes that 3-hydroxyadipic acid-3,6-lactone can be synthesized from an aqueous 3-hydroxyadipic acid solution and the 3-hydroxyadipic acid-3,6-lactone serves as an ε-caprolactam synthesis raw material and, therefore, it may be conceived to recover 3-hydroxyadipic acid-3,6-lactone as an equivalent ε-caprolactam synthesis raw material from a 3-hydroxyadipic acid-containing aqueous solution. However, the recovery method using column chromatography described in WO 2016/068108 is industrially disadvantageous in that the large-scale processing is uneconomical. In addition, 3-hydroxyadipic acid-3,6-lactone and muconolactone have a similar chemical structure but differ in their physical properties (melting point, water solubility and the like), and it is therefore apparent that 3-hydroxyadipic acid-3,6-lactone cannot always be efficiently recovered according to the muconolactone recovery method described in JP-A-2012-000059. In this way, even when recovery of 3-hydroxyadipic acid-3,6-lactone as an equivalent ε-caprolactam synthesis raw material from a 3-hydroxyadipic acid-containing aqueous solution is conceived, recovery of 3-hydroxyadipic acid-3,6-lactone from a 3-hydroxyadipic acid-containing aqueous solution by method using extraction which is industrially advantageous is unprecedented, and there is not known any precedent clearly suggesting a method of implementing the recovery.

SUMMARY

We used 3-hydroxyadipic acid or 3-hydroxyadipic acid-3,6-lactone as a raw material for the synthesis of ε-caprolactam and, as a result, found a method capable of easily recovering 3-hydroxyadipic acid-3,6-lactone when using a 3-hydroxyadipic acid-containing aqueous solution as a raw material.

We thus provide (1) to (6):

(1) A method of producing 3-hydroxyadipic acid-3,6-lactone, the method including the following steps (A) and (B):
(A) a step of adding an acid to a 3-hydroxyadipic acid-containing aqueous solution to obtain a 3-hydroxyadipic acid-3,6-lactone-containing aqueous solution; and
(B) a step of obtaining a 3-hydroxyadipic acid-3,6-lactone extract by bringing the 3-hydroxyadipic acid-3,6-lactone-containing aqueous solution obtained in step (A) into contact with an extraction solvent that is phase-separated from the solution;
(2) The method according to (1), further including step (C) of removing the extraction solvent from the 3-hydroxyadipic acid-3,6-lactone extract obtained in step (B);
(3) The method according to (1) or (2), in which a pH of the 3-hydroxyadipic acid-containing aqueous solution and/or the 3-hydroxyadipic acid-3,6-lactone-containing aqueous solution is adjusted to 4.5 or less;
(4) The method according to any of (1) to (3), in which the 3-hydroxyadipic acid-containing aqueous solution is a 3-hydroxyadipic acid fermentation broth;
(5) The method according to (4), in which step (A) further includes a step of removing microbial cell bodies and/or proteins from the 3-hydroxyadipic acid fermentation broth and/or a 3-hydroxyadipic acid-3,6-lactone-containing aqueous solution obtained from the 3-hydroxyadipic acid fermentation broth;

(6) The method according to (4) or (5), in which step (A) further includes a step of passing the 3-hydroxyadipic acid-3,6-lactone-containing aqueous solution obtained from the 3-hydroxyadipic acid fermentation broth through a nanofiltration membrane and recovering a 3-hydroxyadipic acid-3,6-lactone-containing aqueous solution from a permeate side.

3-hydroxyadipic acid-3,6-lactone serving as an ε-caprolactam synthesis raw material can thus be produced from a 3-hydroxyadipic acid-containing aqueous solution by a method using extraction which is industrially advantageous.

DETAILED DESCRIPTION

Our methods are described in more detail below, but this disclosure is not limited to the following examples.

Step (A)

First, as step (A), an acid is added to a 3-hydroxyadipic acid-containing aqueous solution to obtain a 3-hydroxyadipic acid-3,6-lactone-containing aqueous solution.

The 3-hydroxyadipic acid-containing aqueous solution means an aqueous solution in which 3-hydroxyadipic acid is dissolved. The 3-hydroxyadipic acid in the 3-hydroxyadipic acid-containing aqueous solution may be dissolved in water as a carboxylic acid or a salt thereof. Examples of the salt of the carboxylic acid include a 3-hydroxyadipic acid monolithium salt, a 3-hydroxyadipic acid dilithium salt, a 3-hydroxyadipic acid monosodium salt, a 3-hydroxyadipic acid disodium salt, a 3-hydroxyadipic acid monopotassium salt, a 3-hydroxyadipic acid dipotassium salt, a 3-hydroxyadipic acid magnesium salt, a 3-hydroxyadipic acid calcium salt, a 3-hydroxyadipic acid monoammonium salt, and a 3-hydroxyadipic acid diammonium salt. A mixture of different salts among these may also be used. A trace amount of 3-hydroxyadipic acid-3,6-lactone is sometimes spontaneously produced from 3-hydroxyadipic acid at a stage before intentionally adding an acid to the 3-hydroxyadipic acid-containing aqueous solution. The 3-hydroxyadipic acid-containing aqueous solution may contain a trace amount of 3-hydroxyadipic acid-3,6-lactone produced in this way.

The 3-hydroxyadipic acid-3,6-lactone-containing aqueous solution means an aqueous solution in which 3-hydroxyadipic acid-3,6-lactone produced from part or all of 3-hydroxyadipic acid in the aqueous solution is dissolved due to the addition of an acid to the 3-hydroxyadipic acid-containing aqueous solution. When 3-hydroxyadipic acid-3,6-lactone is produced from part of 3-hydroxyadipic acid, an aqueous solution containing both 3-hydroxyadipic acid and 3-hydroxyadipic acid-3,6-lactone is produced, but the aqueous solution is a 3-hydroxyadipic acid-3,6-lactone-containing aqueous solution.

The 3-hydroxyadipic acid-3,6-lactone in the 3-hydroxyadipic acid-3,6-lactone-containing aqueous solution may be dissolved in water as a carboxylic acid or a salt thereof. Examples of the salt of the carboxylic acid include a 3-hydroxyadipic acid-3,6-lactone lithium salt, a 3-hydroxyadipic acid-3,6-lactone sodium salt, a 3-hydroxyadipic acid-3,6-lactone potassium salt, a 3-hydroxyadipic acid-3,6-lactone magnesium salt, a 3-hydroxyadipic acid-3,6-lactone calcium salt, and a 3-hydroxyadipic acid-3,6-lactone ammonium salt. A mixture of different salts among these may also be used.

The 3-hydroxyadipic acid in the 3-hydroxyadipic acid-3,6-lactone-containing aqueous solution may be dissolved in water as a carboxylic acid or a salt thereof. Examples of the salt of the carboxylic acid include a 3-hydroxyadipic acid monolithium salt, a 3-hydroxyadipic acid dilithium salt, a 3-hydroxyadipic acid monosodium salt, a 3-hydroxyadipic acid disodium salt, a 3-hydroxyadipic acid monopotassium salt, a 3-hydroxyadipic acid dipotassium salt, a 3-hydroxyadipic acid magnesium salt, a 3-hydroxyadipic acid calcium salt, a 3-hydroxyadipic acid monoammonium salt, and a 3-hydroxyadipic acid diammonium salt. A mixture of different salts among these may also be used.

The pH range in step (A) is not particularly limited as long as it is a pH of less than 7, which is at acidic conditions. The lower pH of the aqueous solution is preferable as production of 3-hydroxyadipic acid-3,6-lactone tends to be promoted, but corrosion of an apparatus associated with low pH conditions needs to be taken into account. Considering these factors, the aqueous solution is preferably at a pH of 4.5 or less, more preferably at a pH of 1.5 or more and 4.5 or less, still more preferably at a pH of 2.0 or more and 4.0 or less.

The acid added to the 3-hydroxyadipic acid-containing aqueous solution is not particularly limited as long as it can render the pH acidic. A mineral acid such as sulfuric acid, hydrochloric acid, nitric acid, phosphoric acid and boric acid, or an organic acid such as formic acid, acetic acid and propionic acid, can be favorably used.

The reaction temperature in step (A) is not particularly limited. Although as the reaction temperature is higher, production of 3-hydroxyadipic acid-3,6-lactone tends to be promoted, if the reaction temperature is too high, there is a concern for the production of impurities or corrosion of the apparatus. Considering these factors, the reaction temperature in step (A) is preferably 5° C. or more and 100° C. or less, more preferably 10° C. or more and 90° C. or less, still more preferably 20° C. or more and 80° C. or less.

The 3-hydroxyadipic acid-containing aqueous solution may be an aqueous solution containing 3-hydroxyadipic acid obtained in the process of chemically producing 3-hydroxyadipic acid by an organic synthesis method known to one skilled in the art, or a 3-hydroxyadipic acid fermentation broth obtained in the process of producing 3-hydroxyadipic acid by microbial fermentation disclosed in WO 2017/209102. In addition, the aqueous solution may also be prepared by adding an organochemically or biologically synthesized 3-hydroxyadipic acid or a salt thereof to an aqueous solution.

When the 3-hydroxyadipic acid-containing aqueous solution is a 3-hydroxyadipic acid fermentation broth, it is preferable to remove microbial cell bodies and proteins in the fermentation broth in a step before step (A) or a step after step (A).

As the method of removing microbial cell bodies, for example, a 3-hydroxyadipic acid fermentation broth or a 3-hydroxyadipic acid-3,6-lactone-containing aqueous solution obtained by subjecting the fermentation broth to step (A) is passed through a microfiltration membrane (MF membrane), and a microbial cell body-removed 3-hydroxyadipic acid-containing aqueous solution or 3-hydroxyadipic acid-3,6-lactone-containing aqueous solution can thereby be obtained from the permeate side. Alternatively, a 3-hydroxyadipic acid fermentation broth or a 3-hydroxyadipic acid-3,6-lactone-containing aqueous solution obtained by subjecting the fermentation broth to step (A) is centrifugally treated to spin down microbial cell bodies, and a microbial cell body-removed 3-hydroxyadipic acid-containing aqueous solution or 3-hydroxyadipic acid-3,6-lactone-containing aqueous solution can be obtained by recovering the supernatant.

As the method of removing proteins, for example, a 3-hydroxyadipic acid fermentation broth or a 3-hydroxyadipic acid-3,6-lactone-containing aqueous solution obtained by subjecting the fermentation broth to step (A) is passed through an ultrafiltration membrane (UF membrane), and a protein-removed 3-hydroxyadipic acid-containing aqueous solution or 3-hydroxyadipic acid-3,6-lactone-containing aqueous solution can thereby be obtained from the permeate side.

The order of removing microbial cell bodies and/or proteins is not particularly limited, but it is preferable to first remove microbial cell bodies having a large size, because clogging of an ultrafiltration membrane can be prevented at the time of removing proteins.

When the 3-hydroxyadipic acid-containing aqueous solution is a 3-hydroxyadipic acid fermentation broth, the 3-hydroxyadipic acid-3,6-lactone-containing aqueous solution obtained in step (A) is preferably passed through a nanofiltration membrane (NF membrane) before subjected to step (B). "Passed through a nanofiltration membrane" means that the 3-hydroxyadipic acid-3,6-lactone-containing aqueous solution is passed through a nanofiltration membrane and a 3-hydroxyadipic acid-3,6-lactone-containing aqueous solution is recovered from the permeate side. Due to passing through a nanofiltration membrane, in step (B), after the 3-hydroxyadipic acid-3,6-lactone-containing aqueous solution is brought into contact with an extraction solvent, an insoluble phase (intermediate phase) containing solid matter is prevented from being generated at the phase interface between the 3-hydroxyadipic acid-3,6-lactone-containing aqueous solution and the extraction solvent, and thus phase separation of the 3-hydroxyadipic acid-3,6-lactone-containing aqueous solution from the extraction solvent smoothly occurs.

JP-A-S62-277349 describes that in extracting an amino acid contained in an amino acid fermentation broth into an extraction solvent, when the amino acid fermentation broth is, in a step before extraction, passed through an ultrafiltration membrane (UF membrane) allowing permeation of molecules having a molecular weight of 1,000 or less, phase separation of the amino acid fermentation broth from the extraction solvent occurs clearly and quickly, but use of a nanofiltration membrane is not described. JP-A-2015-119738 describes that in extracting an aliphatic dicarboxylic acid contained in an aliphatic dicarboxylic acid fermentation broth into an extraction solvent, when the fermentation broth is passed through a microfiltration membrane (MF membrane) in a step before extraction, the intermediate insoluble matter generated at the phase interface between the aliphatic dicarboxylic acid fermentation broth and the extraction solvent decreases and the phase-splitting time required for phase separation is shortened. The same publication describes that the membrane used for membrane filtration is preferably a microfiltration membrane or an ultrafiltration membrane and is more preferably a microfiltration membrane, but use of a nanofiltration membrane is not described. It is not easy for one skilled in the art to arrive at, from those descriptions, the effect that when an aqueous carboxylic acid solution having passed through a microfiltration membrane and an ultrafiltration membrane is passed through a nanofiltration membrane, in step (B), generation of an intermediate phase is suppressed and phase separation is promoted, as described in Examples below.

As for the material of the nanofiltration membrane, a polymeric material such as cellulose acetate-based polymer, polyamide, polyester, polyimide and vinyl polymer can be used. The membrane is not limited to a membrane composed of one kind of a material among them and may be a membrane containing a plurality of membrane materials. Also, the membrane structure may be either an asymmetric membrane having a dense layer on at least one surface of the membrane and having micropores with a pore size gradually increasing toward the inside or another surface of the membrane from the dense layer, or a composite membrane having, on the dense layer of the asymmetric membrane, a very thin functional layer formed from other materials. As the composite membrane, for example, a composite membrane described in JP-A-S62-201606, in which a nanofiltration membrane composed of a polyamide functional layer is formed on a support membrane including polysulfone as a membrane material, may be used.

Among these, a composite membrane using polyamide as a functional layer which has all of high pressure resistance, high water permeability and high solute removal performance and exhibits an excellent potential is preferred. Furthermore, to enable maintaining durability against operation pressure, high water permeability and rejection performance, a membrane having a structure in which polyamide is used as the functional layer and the functional layer is held by a support made of a porous membrane or a nonwoven fabric, is preferred. In the nanofiltration membrane using polyamide as a functional layer, the preferable carboxylic acid component that is a monomer constituting the polyamide includes, for example, an aromatic carboxylic acid such as trimesic acid, benzophenone tetracarboxylic acid, trimellitic acid, pyromellitic acid, isophthalic acid, terephthalic acid, naphthalenedicarboxylic acid, diphenylcarboxylic acid and pyridine carboxylic acid. In consideration of solubility for a membrane-forming solvent, trimesic acid, isophthalic acid, terephthalic acid, or a mixture thereof is more preferred.

The preferable amine component that is a monomer constituting the polyamide includes a primary diamine having an aromatic ring such as m-phenylenediamine, p-phenylenediamine, benzidine, methylenebisdianiline, 4,4'-diaminobiphenyl ether, dianisidine, 3,3',4-triaminobiphenyl ether, 3,3',4,4'-tetraminobiphenyl ether, 3,3'-dioxybenzidine, 1,8-naphthalenediamine, m(p)-monomethylphenylenediamine, 3,3'-monomethylamino-4,4'-diaminobiphenyl ether, 4,N,N'-(4-aminobenzoyl)-p(m)-phenylenediamine-2,2'-bis (4-aminophenylbenzimidazole), 2,2'-bis(4-aminophenylbenzoxazole) and 2,2'-bis(4-aminophenylbenzothiazole), and a secondary diamine such as piperazine, piperidine and derivatives thereof. Among them, a nanofiltration membrane using, for the functional layer, a crosslinked polyamide containing piperazine or piperidine as a monomer has heat resistance and chemical resistance, in addition to pressure resistance and durability and, therefore, is preferably used. A nanofiltration membrane containing the crosslinked piperazine polyamide or containing the crosslinked piperidine polyamide as a main component is more preferred. The nanofiltration membrane using the polyamide containing piperazine polyamide for the functional layer includes, for example, those described in JP-A-S62-201606, and specific examples thereof include crosslinked piperazine polyamide-based semipermeable membranes UTC-60 and UTC-63 manufactured by Toray Industries, Inc.

As the spiral-wound nanofiltration membrane element, for example, nanofilter modules SU-210, SU-220, SU-600, and SU-610 manufactured by Toray Industries, Inc. using crosslinked piperazine polyamide for the functional layer and including UTC-60 or UTC-63 manufactured by the same company can also be used. Other examples include NF-45, NF-90, NF-200 and NF-400, which are nanofiltration membranes manufactured by Filmtec Corporation using a crosslinked piperazine polyamide for the functional layer; NF99, NF97 and NF99HF, which are nanofiltration membranes manufactured by Alfa-Laval using polyamide for the functional layer; and GEsepa which is a cellulose acetate-based nanofiltration membrane manufactured by GE Osmonics.

Filtration of the 3-hydroxyadipic acid-3,6-lactone-containing aqueous solution through a nanofiltration membrane may be performed under pressure. The filtration pressure is not particularly limited, but a pressure of 0.1 MPa or more and 8 MPa or less is preferably used, because if the filtration pressure is less than 0.1 MPa, the membrane permeation rate decreases and if it is more than 8 MPa, this affects damage of the membrane. A filtration pressure of 0.5 MPa or more and 7 MPa or less is more preferable as the membrane permeation flux is high and in turn, permeation of 3-hydroxyadipic acid and 3-hydroxyadipic acid-3,6-lactone can be efficiently performed.

As for the filtration of the 3-hydroxyadipic acid-3,6-lactone-containing aqueous solution through a nanofiltration membrane, the recovery rate of 3-hydroxyadipic acid and 3-hydroxyadipic acid-3,6-lactone can be enhanced by returning the non-permeated liquid again to raw water and repeatedly filtering the solution.

Since the nanofiltration membrane has a property of readily allowing permeation of non-ionized (undissociated) substances in the solution, compared to ionized (dissociated) substances, when the pH of the 3-hydroxyadipic acid-3,6-lactone-containing aqueous solution is rendered acidic, the number of 3-hydroxyadipic acid-3,6-lactone in the state of not carboxylate but carboxylic acid increases and permeation through the nanofiltration membrane is facilitated. On the other hand, if the pH is too low, a risk of corrosion of an apparatus arises, and this is industrially disadvantageous. From these viewpoints, the pH of the 3-hydroxyadipic acid-3,6-lactone-containing aqueous solution to be passed through the nanofiltration membrane is preferably adjusted to a pH of 4.5 or less, more preferably to a pH of 1.5 or more and 4.5 or less, still more preferably to a pH of 2.0 or more and 4.0 or less. The acid used when adjusting the pH of the 3-hydroxyadipic acid-3,6-lactone-containing aqueous solution to be passed through the nanofiltration membrane is not particularly limited as long as the pH can be rendered acidic. A mineral acid such as sulfuric acid, hydrochloric acid, nitric acid, phosphoric acid and boric acid, and an organic acid such as formic acid, acetic acid and propionic acid, which are favorably used as the acid in step (A), can be preferably used.

Step (B)

As step (B), a 3-hydroxyadipic acid-3,6-lactone extract is obtained by bringing the 3-hydroxyadipic acid-3,6-lactone-containing aqueous solution obtained in step (A) into contact with an extraction solvent that is phase-separated from the aqueous solution.

The extraction solvent used in step (B) is not particularly limited as long as it undergoes phase separation with respect to the 3-hydroxyadipic acid-3,6-lactone-containing aqueous solution obtained in step (A) and 3-hydroxyadipic acid-3,6-lactone can be extracted. Examples thereof include an aliphatic hydrocarbon-based extraction solvent such as pentane, hexane and heptane, an aromatic hydrocarbon-based extraction solvent such as benzene, toluene and xylene, a chlorine-based extraction solvent such as carbon tetrachloride, chloroform, dichloromethane and trichloroethylene, an ester-based extraction solvent such as ethyl acetate and butyl acetate, a ketone-based extraction solvent such as methyl ethyl ketone, methyl isobutyl ketone, cyclopentanone and cyclohexanone, an ether-based extraction solvent such as dimethyl ether, diethyl ether, diisopropyl ether and dibutyl ether, an alcohol-based extraction solvent with a carbon number of 4 or more such as butanol, hexanol, octanol, decanol and oleyl alcohol, an isopropanol mixture-based extraction solvent such as chloroform/isopropanol mixed solution, dichloromethane/isopropanol mixed solution and ethyl acetate/isopropanol mixed solution, a long-chain amine-based extraction solvent such as trioctylamine, trinonylamine and tridecylamine, an alkylphosphine oxide-based extraction solvent such as tributylphosphine oxide and trioctylphosphine oxide, and an ion liquid-based extraction solvent such as ammonium-based, imidazolium-based, phosphonium-based, pyridinium-based, pyrrolidinium-based and sulfonium-based. One of these extraction solvents may be used alone, or a mixture of two or more thereof may be used.

When a chloroform/isopropanol mixed solution, a dichloromethane/isopropanol mixed solution or an ethyl acetate/isopropanol mixed solution is used as the extraction solvent, the mixing ratio of isopropanol is preferably 40 vol % or less. If the mixing ratio of isopropanol is large, phase separation property in the 3-hydroxyadipic acid-3,6-lactone-containing aqueous solution tends to be reduced.

The extraction temperature in step (B) is not particularly limited but is preferably in a temperature range allowing for no solidification or no boiling of the 3-hydroxyadipic acid-3,6-lactone-containing aqueous solution and the extraction solvent, and from the viewpoint that 3-hydroxyadipic acid-3,6-lactone is easily produced from 3-hydroxyadipic acid, the extraction temperature is more preferably 5° C. or more and 100° C. or less, still more preferably 10° C. or more and 90° C. or less, yet still more preferably 20° C. or more and 80° C. or less. Adjustment of the extraction temperature to such a temperature range facilitates movement of 3-hydroxyadipic acid-3,6-lactone from the 3-hydroxyadipic acid-3,6-lactone-containing aqueous solution to the extraction solvent, and the chemical equilibrium between 3-hydroxyadipic acid and 3-hydroxyadipic acid-3,6-lactone consequently moves toward 3-hydroxyadipic acid-3,6-lactone, as a result, 3-hydroxyadipic acid-3,6-lactone is likely to be produced from 3-hydroxyadipic acid contained in the 3-hydroxyadipic acid-3,6-lactone-containing aqueous solution.

In step (B), the pH of the 3-hydroxyadipic acid-3,6-lactone-containing aqueous solution is not particularly limited as long as it is a pH of less than 7, which is at acidic conditions. Since 3-hydroxyadipic acid-3,6-lactone in the state of not carboxylate but carboxylic acid tends to be more extracted into the extraction solvent, the pH is preferably lower. On the other hand, if the pH is too low, a risk of corrosion of an apparatus arises, and this is industrially disadvantageous. From these viewpoints, the pH of the 3-hydroxyadipic acid-3,6-lactone-containing aqueous solution in step (B) is preferably adjusted to a pH of 4.5 or less, more preferably to a pH of 1.5 or more and 4.5 or less, still more preferably to a pH of 2.0 or more and 4.0 or less. When the pH of the aqueous solution is thus adjusted to be low, as described above, production of 3-hydroxyadipic acid-3,6-lactone from unchanged 3-hydroxyadipic acid in water phase is promoted so that 3-hydroxyadipic acid-3,6-lactone in carboxylic acid state can be kept at a high concentration and can maintain the state of being readily extracted into the extraction solvent.

The acid used when adjusting the pH of the 3-hydroxyadipic acid-3,6-lactone-containing aqueous solution used in step (B) is not particularly limited as long as the pH can be rendered acidic. A mineral acid such as sulfuric acid, hydrochloric acid, nitric acid, phosphoric acid and boric acid, and an organic acid such as formic acid, acetic acid and propionic acid, which are favorably used for pH adjustment in step (A), can be preferably used.

The concentration of 3-hydroxyadipic acid-3,6-lactone in the 3-hydroxyadipic acid-3,6-lactone-containing aqueous solution used in step (B) is not particularly limited, but as the concentration is higher, 3-hydroxyadipic acid-3,6-lactone tends to more readily move to the extraction solvent. Specifically, the concentration is preferably 0.01 wt % or more, more preferably 0.1 wt % or more, still more preferably 1 wt % or more, yet still more preferably 20 wt % or more. As the method of increasing the concentration of the 3-hydroxyadipic acid-3,6-lactone-containing aqueous solution, that is, the method of concentrating the aqueous solution, an evaporation concentration method of removing water by evaporation, a reverse osmosis membrane concentration method of removing water by passing the aqueous solution through a reverse osmosis membrane, or a combination of these methods may be used. The concentration of the 3-hydroxyadipic acid-3,6-lactone-containing aqueous solution may be adjusted to a desired concentration by appropriately controlling the concentration of the 3-hydroxyadipic acid-containing solution used in step (A).

When a raffinate that is a water phase after extracting 3-hydroxyadipic acid-3,6-lactone with an extraction solvent is brought into contact with a fresh extraction solvent, 3-hydroxyadipic acid-3,6-lactone remaining in the raffinate can further be recovered, and the recovery rate of 3-hydroxyadipic acid-3,6-lactone can be increased. The raffinate in which the concentration of 3-hydroxyadipic acid-3,6-lactone is sufficiently reduced may be used as water for adjusting the 3-hydroxyadipic acid-containing aqueous solution or may be purged out of the system.

The extraction may be performed by batch extraction, co-current multiple extraction, countercurrent multi-stage extraction and the like. To continuously perform the extraction in an industrial scale, a mixer settler-type extraction apparatus or a column-type extraction apparatus such as perforated plate extraction column, pulse column and mixer settler column, can be used.

Step (C)

The step of removing the extraction solvent from the 3-hydroxyadipic acid-3,6-lactone extract obtained in step (B) is referred to as step (C).

In step (C), as the method of removing the extraction solvent from the 3-hydroxyadipic acid-3,6-lactone extract, a general method, for example, a method of evaporatively concentrating the extraction solvent from the extract, a method of precipitating 3-hydroxyadipic acid-3,6-lactone from the extract and then performing solid-liquid separation to separate the extraction solvent, and a method of bringing the extract into contact with an aqueous solution to back-extract 3-hydroxyadipic acid-3,6-lactone into a water phase and separating the water phase to thereby perform separation between 3-hydroxyadipic acid-3,6-lactone and the extraction solvent, may be used.

The extraction solvent removed from the extract may be directly recycled as the extraction solvent in step (B) or may be purified by distillation and then recycled as the extraction solvent in step (B). In purifying the extraction solvent by distillation, the recovered amount of 3-hydroxyadipic acid-3,6-lactone can be increased by recovering a trace amount of 3-hydroxyadipic acid-3,6-lactone contained in the extraction solvent.

Other Steps

When the 3-hydroxyadipic acid-containing aqueous solution used in step (A), the 3-hydroxyadipic acid-3,6-lactone-containing aqueous solution used in step (B), and a dilute aqueous 3-hydroxyadipic acid-3,6-lactone solution obtained by back extraction with water of the 3-hydroxyadipic acid-3,6-lactone extract in step (C) are passed through a reverse osmosis membrane (RO membrane), 3-hydroxyadipic acid and 3-hydroxyadipic acid-3,6-lactone can be concentrated. "Passed through a reverse osmosis membrane" means that the aqueous solution is filtered through a reverse osmosis membrane and after water is removed from the permeate side, an aqueous solution having increased concentrations of 3-hydroxyadipic acid and 3-hydroxyadipic acid-3,6-lactone is recovered from the non-permeate side.

As the membrane material of the reverse osmosis membrane, a commonly commercially available polymeric material such as cellulose acetate-based polymer, polyamide, polyester, polyimide and vinyl polymer can be used, but the membrane is not limited to a membrane composed of one kind of a material among them and may be a membrane containing a plurality of membrane materials. As for the shape of the membrane, a membrane having an appropriate shape such as flat membrane type, spiral type and hollow fiber type can be used.

Specific examples of the reverse osmosis membrane include polyamide-based reverse osmosis membranes (UTC) SU-710, SU-720, SU-720F, SU-710L, SU-720L, SU-720LF, SU-720R, SU-710P, SU-720P, SU-810, SU-820, SU-820L, and SU-820FA manufactured by Toray Industries, Inc.; cellulose acetate-based reverse osmosis membranes SC-L100R, SC-L200R, SC-1100, SC-1200, SC-2100, SC-2200, SC-3100, SC-3200, SC-8100, and SC-8200 manufactured by the same company; NTR-759HR, NTR-729HF, NTR-70SWC, ES10-D, ES20-D, ES20-U, ES15-D, ES15-U, and LF10-D manufactured by Nitto Denko Corporation; RO98pHt, R099, HR98PP, and CE4040C-30D manufactured by Alfa-Laval; GE Sepa manufactured by GE; and BW30-4040, TW30-4040, XLE-4040, LP-4040, LE-4040, SW30-4040, and SW30HRLE-4040 manufactured by Filmtec.

Filtration with a reverse osmosis membrane is performed under pressure, and the filtration pressure is preferably 1 MPa or more and 8 MPa or less, because if the filtration pressure is less than 1 MPa, the membrane permeation rate decreases and if it is more than 8 MPa, this affects damage of the membrane. The filtration pressure is more preferably 1 MPa or more and 7 MPa or less, still more preferably 2 MPa or more and 6 MPa or less.

EXAMPLES

Our methods are described in more detail below by referring to Reference Examples, Comparative Reference Examples and Examples, but this disclosure is not limited to these results.

HPLC Analysis Conditions

HPLC Analysis was performed under the following analysis conditions.

Column 1: Synergi Polar-RP (manufactured by Phenomenex Inc.)
Column 2: Synergi Hydro-RP (manufactured by Phenomenex Inc.)
Column temperature: 45° C.
Mobile phase 1: aqueous 5 mM formic acid solution/acetonitrile=98/2 (vol/vol), 1 mL/min
Mobile phase 2: aqueous (5 mM formic acid, 20 mM Bis-Tris, 0.1 mM EDTA-2Na) solution/acetonitrile=98/2 (vol/vol), 1 mL/min
Detection: electric conductivity pH Analysis Method Horiba pH Meter F-52 (manufactured by Horiba Ltd.) was used. The pH calibration was performed using a standard pH 4.01 solution (produced by FUJIFILM Wako Pure Chemical Corporation), a standard pH 6.86 solution (produced by FUJIFILM Wako Pure Chemical Corporation), and a standard pH 9.18 solution (produced by FUJIFILM Wako Pure Chemical Corporation).

Reference Example 1 Preparation of 3-Hydroxyadipic Acid-Containing Aqueous Solution 100 L of a 3-hydroxyadipic acid fermentation broth was prepared according to the method using *Serratia grimesii* (NBRC13537)/pBBR1MCS-2::CgpcaF described in Example 14 of WO 2017/209102. The supernatant was analyzed by HPLC. The 3-hydroxyadipic acid concentration was 50 mg/L.

Reference Example 2 Preparation of 3-hydroxyadipic acid-3,6-lactone

3-Hydroxyadipic acid-3,6-lactone used in Reference Examples 8 to 19 was prepared by chemical synthesis. First, 1.5 L of anhydrous tetrahydrofuran (produced by FUJIFILM Wako Pure Chemical Corporation) was added to 13.2 g (0.1 mol) of succinic acid monomethyl ester (produced by FUJIFILM Wako Pure Chemical Corporation), and 16.2 g (0.1 mol) of carbonyldiimidazole (produced by FUJIFILM Wako Pure Chemical Corporation) was added thereto with stirring, followed by stirring at room temperature for 1 hour under nitrogen atmosphere. To the obtained suspension, 15.6 g (0.1 mol) of malonic acid monomethyl ester potassium salt and 9.5 g (0.1 mol) of magnesium chloride were added, and the resulting mixture was stirred at room temperature for 1 hour under nitrogen atmosphere and then stirred at 40° C. for 12 hours. After completion of the reaction, 0.05 L of 1 mol/L hydrochloric acid was added, and the resulting mixture was subjected to extraction with ethyl acetate and then subjected to separation purification by silica gel column chromatography (hexane:ethyl acetate=1:5) to obtain 13.1 g of pure 3-oxohexanedicarboxylic acid dimethyl ester.

0.1 L of methanol (produced by Kokusan Chemical Co., Ltd.) was added to 10 g (0.05 mol) of the obtained 3-oxohexanedicarboxylic acid dimethyl ester, and 0.02 L of an aqueous 5 mol/L sodium hydroxide solution was added thereto with stirring, followed by stirring at room temperature for 2 hours. After completion of the reaction, the pH was adjusted to 1 with 5 mol/L hydrochloric acid and subsequently, 2.0 g (0.05 mol) of sodium borohydride (produced by FUJIFILM Wako Pure Chemical Corporation) was added thereto, followed by stirring at room temperature for 2 hours. After the resulting reaction solution was concentrated using a rotary evaporator, 0.1 L of ultrapure water was added, and 0.01 L of 1 mol/L sulfuric acid was added thereto with stirring, followed by stirring at 100° C. for 2 hours. After completion of the reaction, the reaction solution was concentrated using a rotary evaporator and then subjected to separation purification by silica gel column chromatography (chloroform:methanol=10:1) to obtain 5.8 g of pure 3-hydroxyadipic acid-3,6-lactone (in light yellow syrup form). The NMR spectrum of the obtained 3-hydroxyadipic acid-3,6-lactone is as follows.

$^1$H-NMR (400 MHz, D$_2$O): δ2.03 (m, 1H), δ2.04-2.90 (m, 5H), δ5.00 (m, 1H)

Reference Example 3

The 3-hydroxyadipic acid fermentation broth obtained in Reference Example 1 was passed through a microfiltration membrane (a porous membrane having a pore size of 0.01 μm or more and less than 1 μm; manufactured by Toray Industries, Inc.) and then passed through an ultrafiltration membrane (molecular weight cut off: 10,000; manufactured by Toray Industries, Inc.), and 100 L of the 3-hydroxyadipic acid fermentation broth having passed through the microfiltration membrane and the ultrafiltration membrane was concentrated 100 times using a rotary evaporator (manufactured by Tokyo Rikakikai Co., Ltd.) to obtain 1 L of a concentrated solution. The pH was adjusted to 4.0 by the addition of concentrated sulfuric acid (produced by Sigma-Aldrich) to 10 mL of the concentrated solution, the solution was stirred at room temperature (25° C.) for 12 hours, and then the supernatant was analyzed by HPLC. The concentration ratio between 3-hydroxyadipic acid and 3-hydroxyadipic acid-3,6-lactone (3-hydroxyadipic acid-3,6-lactone/3-hydroxyadipic acid) is shown in Table 1.

Reference Example 4

The experiment was performed in the same manner as in Reference Example 3 except that the pH of the concentrated solution was adjusted to 2.0. The result is shown in Table 1.

Reference Example 5

The experiment was performed in the same manner as in Reference Example 3 except that the pH of the concentrated solution was adjusted to 1.0. The result is shown in Table 1.

Reference Example 6

The experiment was performed in the same manner as in Reference Example 3 except that the pH of the concentrated solution was adjusted to 2.0 and then the solution was stirred at 70° C. for 3 hours. The result is shown in Table 1.

Reference Example 7

The experiment was performed in the same manner as in Reference Example 3 except that the pH of the concentrated solution was adjusted to 2.0 and then the solution was stirred at 70° C. for 12 hours. The result is shown in Table 1.

Comparative Reference Example 1

The experiment was performed in the same manner as in Reference Example 3 except that an acid was not added to the concentrated solution (pH: 6.5). The result is shown in Table 1.

TABLE 1

|  | pH | Temperature (° C.) | Stirring Time (hr) | 3HAL/3HA (mol/mol) |
|---|---|---|---|---|
| Reference Example 3 | 4.0 | room temperature | 12 | 0.82 |
| Reference Example 4 | 2.0 | room temperature | 12 | 2.48 |
| Reference Example 5 | 1.0 | room temperature | 12 | 3.97 |

TABLE 1-continued

|  | pH | Temperature (° C.) | Stirring Time (hr) | 3HAL/3HA (mol/mol) |
|---|---|---|---|---|
| Reference Example 6 | 2.0 | 70 | 3 | 5.41 |
| Reference Example 7 | 1.0 | 70 | 3 | 9.27 |
| Comparative Reference Example 1 | 6.5 (no addition of acid) | room temperature | 12 | 0 |

Reference Examples 3 to 7 reveal that a 3-hydroxyadipic acid-3,6-lactone-containing aqueous solution is obtained by adding an acid to a 3-hydroxyadipic acid-containing aqueous solution. Also, Reference Examples 3 to 7 reveal that as the pH is lower, the 3-hydroxyadipic acid-3,6-lactone concentration increases. In addition, as the reaction temperature is higher, the 3-hydroxyadipic acid-3,6-lactone concentration is increased in a shorter time. On the other hand, Comparative Reference Example 1 reveals that when an acid is not added, a 3-hydroxyadipic acid-3,6-lactone-containing aqueous solution cannot be obtained.

Reference Examples 8 to 15

A 3-hydroxyadipic acid-3,6-lactone-containing aqueous solution (pH: 2.1) having an initial concentration of 3-hydroxyadipic acid-3,6-lactone of 200 g/L was prepared using 3-hydroxyadipic acid-3,6-lactone prepared in Reference Example 2. 0.5 mL of the aqueous solution and 0.5 mL of various extraction solvents were added to a 2 mL Eppendorf tube, and the tube was shaken at 1,500 rpm for 1 hour at room temperature using Cute Mixer CM-1000 (manufactured by Tokyo Rikakikai Co., Ltd.). After shaking, the 3-hydroxyadipic acid-3,6-lactone concentration in water phase which is a raffinate was measured by HPLC, and the extraction rate was calculated according to the following formula:

Extraction rate (%)=(1−(concentration of to-be-extracted compound in raffinate)/(concentration of to-be-extracted compound before extraction))×100

Extraction solvents used in respective Reference Examples were dimethyl ether (Reference Example 8), chloroform (Reference Example 9), dichloromethane (Reference Example 10), ethyl acetate (Reference Example 11), butyl acetate (Reference Example 12), a dichloromethane/isopropanol mixed solution (volume ratio: 3/1) (Reference Example 13), 2-octanol (Reference Example 14), and methyl isobutyl ketone (Reference Example 15). All of the extraction solvents used are produced by FUJIFILM Wako Pure Chemical Corporation. The extraction rate of 3-hydroxyadipic acid-3,6-lactone is shown in Table 2.

Reference Examples 16 to 19

The experiments were performed in the same manner as in Reference Examples 10, 11, 13 and 15 except for using a 3-hydroxyadipic acid-3,6-lactone-containing aqueous solution (pH: 2.3) having an initial concentration of 3-hydroxyadipic acid-3,6-lactone of 50 g/L (Reference Examples 16, 17, 18 and 19, respectively). The extraction rate of 3-hydroxyadipic acid-3,6-lactone is shown in Table 2.

TABLE 2

|  | 3-Hydroxyadipic Acid-3,6-Lactone Concentration (g/L) | Extraction Solvent | Extraction Rate (%) |
|---|---|---|---|
| Reference Example 8 | 200 | diethyl ether | 2.4 |
| Reference Example 9 | 200 | chloroform | 3.3 |
| Reference Example 10 | 200 | dichloromethane | 8.4 |
| Reference Example 11 | 200 | ethyl acetate | 36.3 |
| Reference Example 12 | 200 | butyl acetate | 9.6 |
| Reference Example 13 | 200 | dichloromethane/isopropanol mixed solution | 47.5 |
| Reference Example 14 | 200 | 2-octanol | 8.2 |
| Reference Example 15 | 200 | methyl isobutyl ketone | 22.1 |
| Reference Example 16 | 50 | dichloromethane | 13.5 |
| Reference Example 17 | 50 | ethyl acetate | 40.2 |
| Reference Example 18 | 50 | dichloromethane/isopropanol mixed solution | 31.8 |
| Reference Example 19 | 50 | methyl isobutyl ketone | 25.3 |

Reference Example 20

The 3-hydroxyadipic acid fermentation broth obtained in Reference Example 1 was passed through a microfiltration membrane (a porous membrane having a pore size of 0.01 μm or more and less than 1 μm; manufactured by Toray Industries, Inc.) and then passed through an ultrafiltration membrane (molecular weight cut off: 10,000; manufactured by Toray Industries, Inc.), and 100 L of the 3-hydroxyadipic acid fermentation broth having passed through the microfiltration membrane and the ultrafiltration membrane was concentrated 1,000 times using a rotary evaporator (manufactured by Tokyo Rikakikai Co., Ltd.). The pH of the concentrated solution obtained was adjusted to 4.6 by the addition of concentrated sulfuric acid (produced by Sigma-Aldrich) thereto, the solution was stirred for 12 hours, and then water was added to the solution to obtain a 3-hydroxyadipic acid-3,6-lactone-containing aqueous solution in which the 3-hydroxyadipic acid-3,6-lactone concentration is adjusted to 40.0 g/L. By use of this 3-hydroxyadipic acid- 3,6-lactone-containing aqueous solution, an extraction test using ethyl acetate as the extraction solvent was performed in the same manner as in Reference Example 11. The extraction rate of 3-hydroxyadipic acid-3,6-lactone is shown in Table 3.

Reference Example 21

The experiment was performed in the same manner as in Reference Example 20 except that the pH was adjusted to 4.0 instead of being adjusted to 4.6. The result is shown in Table 3.

Reference Example 22

The experiment was performed in the same manner as in Reference Example 20 except that methyl isobutyl ketone was used as the extraction solvent in place of ethyl acetate. The result is shown in Table 3.

Reference Example 23

The experiment was performed in the same manner as in Reference Example 22 except that the pH was adjusted to 4.0. The result is shown in Table 3.

Comparative Reference Example 2

The experiment was performed in the same manner as in Reference Example 20 except that a 3-hydroxyadipic acid-containing aqueous solution obtained without addition of an acid at the time of adjusting the pH to 4.6 in Reference Example 20 was used and methyl isobutyl ketone was used as the extraction solvent in place of ethyl acetate. The extraction rate of 3-hydroxyadipic acid is shown in Table 3.

TABLE 3

| | pH | Extraction Solvent | Extraction Rate (%) |
|---|---|---|---|
| Reference Example 20 | 4.6 | ethyl acetate | 16.3 |
| Reference Example 21 | 4.0 | ethyl acetate | 40.1 |
| Reference Example 22 | 4.6 | methyl isobutyl ketone | 6.8 |
| Reference Example 23 | 4.0 | methyl isobutyl ketone | 22.7 |
| Comparative Reference Example 2 | 6.5 | methyl isobutyl ketone | 0 |

A comparison between Reference Examples 20 and 21 and a comparison between Reference Examples 22 and 23 reveal that when the pH is lower than 4.5, the extraction rate is enhanced. On the other hand, Comparative Reference Example 2 reveals that 3-hydroxyadipic acid is poorly extracted into the extraction solvent.

Example 1

The 3-hydroxyadipic acid fermentation broth obtained in Reference Example 1 was passed through a microfiltration membrane (a porous membrane having a pore size of 0.01 µm or more and less than 1 µm; manufactured by Toray Industries, Inc.) and then passed through an ultrafiltration membrane (molecular weight cut off: 10,000; manufactured by Toray Industries, Inc.), and 100 L of the 3-hydroxyadipic acid fermentation broth having passed through the microfiltration membrane and the ultrafiltration membrane was concentrated 1,000 times using a rotary evaporator (manufactured by Tokyo Rikakikai Co., Ltd.). The pH of the concentrated solution obtained was adjusted to 4.0 by the addition of concentrated sulfuric acid (produced by Sigma-Aldrich) thereto. After stirring for 12 hours, the resulting 3-hydroxyadipic acid-3,6-lactone-containing aqueous solution was transferred to a glass-made separating funnel (volume: 500 mL), and 100 mL of ethyl acetate (produced by FUJIFILM Wako Pure Chemical Corporation) was added thereto, followed by 60 times shaking. After standing still, the ethyl acetate phase was recovered, 100 mL of ethyl acetate was further added to the raffinate, followed by 60 times shaking, and then the ethyl acetate phase was recovered. The same operation was repeated to perform extraction of 3-hydroxyadipic acid-3,6-lactone by use of a total of 1 L of ethyl acetate (extraction rate: 90%). The 3-hydroxyadipic acid-3,6-lactone extract (about 1 L) obtained by recovering the ethyl acetate phase was concentrated using a rotary evaporator to remove ethyl acetate which is the extraction solvent, as a result, 2.1 g of 3-hydroxyadipic acid-3,6-lactone in a dark brown syrup form was obtained.

In this extraction, an intermediate phase containing solid matter was generated between the water phase and the ethyl acetate phase and, therefore, the system had to be left standing still for at least 1 hour or more before starting the next extraction operation.

Example 2

The experiment was performed in the same manner as in Example 1 except that methyl isobutyl ketone was used as the extraction solvent in place of ethyl acetate, and 1.8 g of 3-hydroxyadipic acid-3,6-lactone in a dark brown syrup form was obtained (extraction rate: 80%). In addition, as with Example 1, an intermediate phase containing solid matter was generated between the water phase and the methyl isobutyl ketone phase.

Examples 1 and 2 revealed that 3-hydroxyadipic acid-3,6-lactone can be produced by a method including a step of adding an acid to a 3-hydroxyadipic acid-containing aqueous solution to obtain a 3-hydroxyadipic acid-3,6-lactone-containing aqueous solution, and a step of obtaining a raffinate and a 3-hydroxyadipic acid-3,6-lactone extract by bringing the 3-hydroxyadipic acid-3,6-lactone-containing aqueous solution above into contact with an extraction solvent that is phase-separated from the aqueous solution.

Reference Examples 24 to 27

1 L of the 3-hydroxyadipic acid fermentation broth obtained in Reference Example 1 was passed through a microfiltration membrane (a porous membrane having a pore size of 0.01 µm or more and less than 1 µm; manufactured by Toray Industries, Inc.) and then passed through an ultrafiltration membrane (molecular weight cut off: 10,000; manufactured by Toray Industries, Inc.) and, thereafter, the pH was adjusted to 4.0 by use of concentrated sulfuric acid (produced by Sigma-Aldrich), followed by stirring for 12 hours. The thus-obtained 3-hydroxyadipic acid-3,6-lactone-containing aqueous solution was transferred to a raw water tank and passed through a nanofiltration membrane under nanofiltration membrane treatment conditions 1 below. The obtained permeate was a clear aqueous solution where coloring components were removed. The 3-hydroxyadipic acid concentration and 3-hydroxyadipic acid-3,6-lactone concentration in the permeate were analyzed by HPLC, and the permeation rate was calculated according to the following formula. Calculation results of the permeation rate are shown in Table 4.

Permeation rate (%)=(compound's concentration in permeate)/(compound's concentration in raw water)×100

Nanofiltration Membrane Treatment Conditions 1
Separation membrane: UTC-63 (manufactured by Toray Industries, Inc.)
Membrane separation unit: "SEPA" (registered trademark) CF-II (manufactured by GE W & PT)
Operation temperature: 25° C.
Filtration pressure: from 0.21 to 2.03 MPa Comparative Reference Examples 3 to 6

The experiments were performed in the same manner as in Reference Examples 24 to 27 except for using a 3-hydroxyadipic acid-containing aqueous solution obtained without adding an acid. Calculation results of the permeation rate of 3-hydroxyadipic acid are shown in Table 4. Incidentally, 3-hydroxyadipic acid-3,6-lactone was not produced and therefore, is not applicable to the permeation rate calculation object.

TABLE 4

| | | | Permeation Rate (%) | |
|---|---|---|---|---|
| | pH | Filtration Pressure (MPa) | 3-Hydroxyadipic Acid | 3-Hydroxyadipic Acid-3,6-Lactone |
| Reference Example 24 | 4.0 | 0.21 | 88 | >99 |
| Reference Example 25 | 4.0 | 0.52 | 76 | 93 |
| Reference Example 26 | 4.0 | 0.95 | 43 | 71 |
| Reference Example 27 | 4.0 | 1.99 | 25 | 35 |
| Comparative Reference Example 3 | 6.5 | 0.21 | 11 | N/A |
| Comparative Reference Example 4 | 6.5 | 0.53 | <1 | N/A |
| Comparative Reference Example 5 | 6.5 | 0.84 | <1 | N/A |
| Comparative Reference Example 6 | 6.5 | 1.25 | <1 | N/A |

N/A: not applicable

Reference Examples 24 to 27 reveal that when the pH is adjusted to be acidic by adding an acid, 3-hydroxyadipic acid and 3-hydroxyadipic acid-3,6-lactone permeate through the nanofiltration membrane and a clear 3-hydroxyadipic acid-3,6-lactone-containing aqueous solution is obtained. On the other hand, Comparative Reference Examples 3 to 6 reveal that when an acid is not added, the permeability of 3-hydroxyadipic acid in nanofiltration membrane is significantly reduced.

Example 3

100 L of the 3-hydroxyadipic acid fermentation broth obtained in Reference Example 1 was passed through a microfiltration membrane (a porous membrane having a pore size of 0.01 µm or more and less than 1 µm; manufactured by Toray Industries, Inc.) and then passed through an ultrafiltration membrane (molecular weight cut off: 10,000; manufactured by Toray Industries, Inc.), and the pH was adjusted to 4.0 by the addition of concentrated sulfuric acid (produced by Sigma-Aldrich). After stirring for 12 hours, the resulting 3-hydroxyadipic acid-3,6-lactone-containing aqueous solution was transferred to a raw water tank and passed through a nanofiltration membrane under nanofiltration membrane treatment conditions 2 below. The non-permeated liquid was returned to the raw water tank. When the liquid volume ran short, pure water was added to the raw water tank to continue the nanofiltration membrane treatment, and the total amount of 3-hydroxyadipic acid-3,6-lactone was recovered in the permeate side.

Nanofiltration Membrane Treatment Conditions 2
Separation membrane: UTC-63 (manufactured by Toray Industries, Inc.)
Membrane separation unit: "SEPA" (registered trademark) CF-II (manufactured by GE W & PT)
Operation temperature: 25° C.
Filtration pressure: from 0.5 MPa The permeate of the nanofiltration membrane was concentrated to 100 mL by using a rotary evaporator (manufactured by Tokyo Rikakikai Co., Ltd.), and the pH was adjusted to 4.0 by the addition of concentrated sulfuric acid (produced by Sigma-Aldrich). The resulting 3-hydroxyadipic acid-3,6-lactone-containing aqueous solution was transferred to a glass-made separating funnel (volume: 500 mL), and 100 mL of ethyl acetate (produced by FUJIFILM Wako Pure Chemical Corporation) was added thereto, followed by 60 times shaking. After standing still, the ethyl acetate phase was recovered, 100 mL of ethyl acetate was further added to the raffinate, followed by 60 times shaking, and then the ethyl acetate phase was recovered. The same operation was repeated to perform extraction of 3-hydroxyadipic acid-3,6-lactone by use of a total of 1 L of ethyl acetate (extraction rate: 92%). The 3-hydroxyadipic acid-3,6-lactone extract (about 1 L) obtained by recovering the ethyl acetate phase was concentrated using a rotary evaporator to remove ethyl acetate which is the extraction solvent, as a result, 2.1 g of 3-hydroxyadipic acid-3,6-lactone in a light yellow syrup form was obtained.

In the extraction above, formation of an intermediate phase containing solid matter was substantially not observed between the water phase and the ethyl acetate phase, and phase separation occurred very quickly in dozen seconds so that the next extraction operation could be soon started.

Example 4

The experiment was performed in the same manner as in Example 3 except that methyl isobutyl ketone was used as the extraction solvent in place of ethyl acetate, and 1.9 g of 3-hydroxyadipic acid-3,6-lactone in a light yellow syrup form was obtained. Extraction rate of 3-hydroxyadipic acid-3,6-lactone was 83%. In this extraction as well, formation of an intermediate phase containing solid matter was substantially not observed between the water phase and the methyl isobutyl ketone phase, and phase separation occurred very quickly in dozen seconds.

A comparison between Examples 1 and 3 and a comparison between Examples 2 and 4 reveal that in all Examples, although 3-hydroxyadipic acid-3,6-lactone could be obtained, when the 3-hydroxyadipic acid-3,6-lactone-containing aqueous solution is passed through the nanofiltration membrane, phase separation at the time of performing extraction occurs quickly and the color tone of the obtained 3-hydroxyadipic acid-3,6-lactone becomes closer to that of the chemically synthesized standard sample.

Example 5

The 3-hydroxyadipic acid fermentation broth obtained in Reference Example 1 was passed through a microfiltration membrane (a porous membrane having a pore size of 0.01 µm or more and less than 1 µm; manufactured by Toray Industries, Inc.), and the pH was then adjusted to 4.0 by the addition of concentrated sulfuric acid (produced by Sigma-Aldrich). After stirring for 12 hours, the resulting solution was passed through an ultrafiltration membrane (molecular weight cut off: 10,000; manufactured by Toray Industries, Inc.). After that, concentration, extraction, and removal of extraction solvent were performed in the same manner as in Example 1 to obtain 0.4 g of 3-hydroxyadipic acid-3,6-lactone in a dark yellow syrup form.

In this extraction, an intermediate phase containing solid matter was generated between the water phase and the ethyl acetate phase. The system had to be left standing still for 10 minutes until phase separation clearly occurs.

Example 6

The 3-hydroxyadipic acid fermentation broth obtained in Reference Example 1 was passed through a microfiltration membrane (a porous membrane having a pore size of 0.01 μm or more and less than 1 μm; manufactured by Toray Industries, Inc.), and the pH was then adjusted to 4.0 by the addition of concentrated sulfuric acid (produced by Sigma-Aldrich). After stirring for 12 hours, the resulting solution was passed through an ultrafiltration membrane (molecular weight cut off: 10,000; manufactured by Toray Industries, Inc.). Thus-obtained 100 L of the 3-hydroxyadipic acid-3,6-lactone-containing aqueous solution was concentrated to 100 mL by using a rotary evaporator (manufactured by Tokyo Rikakikai Co., Ltd.). The pH was then adjusted to 3.5 by the addition of concentrated sulfuric acid (produced by Sigma-Aldrich), and after stirring at 70° C. for 3 hours, extraction and removal of extraction solvent were performed in the same manner as in Example 1 to obtain 2.5 g of 3-hydroxyadipic acid-3,6-lactone in a yellow-brown syrup form.

In this extraction, an intermediate phase containing solid matter was generated between the water phase and the ethyl acetate phase. The system had to be left standing still for 10 minutes until phase separation clearly occurs.

Example 7

100 L of the 3-hydroxyadipic acid fermentation broth obtained in Reference Example 1 was passed through a microfiltration membrane (a porous membrane having a pore size of 0.01 μm or more and less than 1 μm; manufactured by Toray Industries, Inc.), and the pH was then adjusted to 4.0 by the addition of concentrated sulfuric acid (produced by Sigma-Aldrich). After stirring for 12 hours, the resulting solution was passed through an ultrafiltration membrane (molecular weight cut off: 10,000; manufactured by Toray Industries, Inc.). The thus-obtained 3-hydroxyadipic acid-3,6-lactone-containing aqueous solution was passed through a nanofiltration membrane under the above-described nanofiltration membrane treatment conditions 2.

The permeate of the nanofiltration membrane was concentrated to 100 mL by using a rotary evaporator (manufactured by Tokyo Rikakikai Co., Ltd.), and the pH was adjusted to 4.0 by the addition of concentrated sulfuric acid (produced by Sigma-Aldrich). After stirring at 80° C. for 12 hours, extraction and removal of extraction solvent were performed in the same manner as in Example 1 to obtain 1.2 g of 3-hydroxyadipic acid-3,6-lactone in a dark brown syrup form.

In this extraction, formation of an intermediate phase containing solid matter was almost not observed between the water phase and the ethyl acetate phase, and phase separation occurred very quickly in dozen seconds.

Example 8

100 L of the 3-hydroxyadipic acid fermentation broth obtained in Reference Example 1 was passed through a microfiltration membrane (a porous membrane having a pore size of 0.01 μm or more and less than 1 μm; manufactured by Toray Industries, Inc.), and the pH was then adjusted to 2.0 by the addition of concentrated sulfuric acid (produced by Sigma-Aldrich). After stirring at 85° C. for 12 hours, the obtained 3-hydroxyadipic acid-3,6-lactone-containing aqueous solution was concentrated to 100 mL by using a rotary evaporator (manufactured by Tokyo Rikakikai Co., Ltd.) and, thereafter, extraction and removal of extraction solvent were performed in the same manner as in Example 1 to obtain 3.0 g of dark orange 3-hydroxyadipic acid-3,6-lactone.

In this extraction, a large amount of an intermediate phase containing solid matter was generated between the water phase and the ethyl acetate phase. The system had to be left standing still for 2 hours until phase separation clearly occurs.

Example 9

100 L of the 3-hydroxyadipic acid fermentation broth obtained in Reference Example 1 was passed through a microfiltration membrane (a porous membrane having a pore size of 0.01 μm or more and less than 1 μm; manufactured by Toray Industries, Inc.), and the pH was then adjusted to 2.0 by the addition of concentrated sulfuric acid (produced by Sigma-Aldrich). After stirring at 85° C. for 12 hours, the resulting solution was passed through an ultrafiltration membrane (molecular weight cut off: 10,000; manufactured by Toray Industries, Inc.) and, thereafter, concentration, extraction, and removal of extraction solvent were performed in the same manner as in Example 8 to obtain 2.8 g of dark orange 3-hydroxyadipic acid-3,6-lactone.

In this extraction, an intermediate phase containing solid matter was generated between the water phase and the ethyl acetate phase. The system had to be left standing still for 10 minutes until phase separation clearly occurs.

Example 10

100 L of the 3-hydroxyadipic acid fermentation broth obtained in Reference Example 1 was passed through a microfiltration membrane (a porous membrane having a pore size of 0.01 μm or more and less than 1 μm; manufactured by Toray Industries, Inc.), and the pH was then adjusted to 2.0 by the addition of concentrated sulfuric acid (produced by Sigma-Aldrich). After stirring at 85° C. for 12 hours, the resulting solution was passed through an ultrafiltration membrane (molecular weight cut off: 10,000; manufactured by Toray Industries, Inc.). The thus-obtained 3-hydroxyadipic acid-3,6-lactone-containing aqueous solution was passed through a nanofiltration membrane under the above-described nanofiltration membrane treatment conditions 2. Thereafter, concentration, extraction, and removal of extraction solvent were performed in the same manner as in Example 8 to obtain 2.9 g of light orange 3-hydroxyadipic acid-3,6-lactone.

In this extraction, formation of an intermediate phase containing solid matter was almost not observed between the water phase and the ethyl acetate phase, and phase separation occurred very quickly in dozen seconds.

Examples 5 to 10 reveal that 3-hydroxyadipic acid-3,6-lactone can be produced without being restricted by the order of pH adjustment by the addition of an acid or heating treatment, and the conditions such as pH after the addition of an acid or heating temperature.

The invention claimed is:

1. A method of producing 3-hydroxyadipic acid-3,6-lactone, the method comprising steps (A) and (B):
   (A) adding an acid to a 3-hydroxyadipic acid-containing aqueous solution to obtain a 3-hydroxyadipic acid-3,6-lactone-containing aqueous solution; and
   (B) obtaining a 3-hydroxyadipic acid-3,6-lactone extract by bringing the 3-hydroxyadipic acid-3,6-lactone-containing aqueous solution obtained in step (A) into contact with an extraction solvent that is phase-separated from the solution.

2. The method according to claim 1, further comprising (C) removing the extraction solvent from the 3-hydroxyadipic acid-3,6-lactone extract obtained in step (B).

3. The method according to claim 1, wherein a pH of the 3-hydroxyadipic acid-containing aqueous solution and/or the 3-hydroxyadipic acid-3,6-lactone-containing aqueous solution is adjusted to 4.5 or less.

4. The method according to claim 1, wherein the 3-hydroxyadipic acid-containing aqueous solution is a 3-hydroxyadipic acid fermentation broth.

5. The method according to claim 4, wherein step (A) further comprises removing microbial cell bodies and/or proteins from the 3-hydroxyadipic acid fermentation broth and/or a 3-hydroxyadipic acid-3,6-lactone-containing aqueous solution obtained from the 3-hydroxyadipic acid fermentation broth.

6. The method according to claim 4, wherein step (A) further comprises passing the 3-hydroxyadipic acid-3,6-lactone-containing aqueous solution obtained from the 3-hydroxyadipic acid fermentation broth through a nanofiltration membrane and recovering a 3-hydroxyadipic acid-3,6-lactone-containing aqueous solution from a permeate side.

* * * * *